United States Patent
Roine et al.

(10) Patent No.: US 9,205,464 B2
(45) Date of Patent: Dec. 8, 2015

(54) ARRANGEMENT AND METHOD FOR MECHANICAL CLEANING OF A TRANSPARENT SURFACE OF AN OPTICAL INSTRUMENT

(75) Inventors: Juho Roine, Helsinki (FI); Gennadi Zaitsev, Hikia (FI)

(73) Assignee: OY, CLEWER, Turku (FI)

( * ) Notice: Subject to any disclaimer, the term of this patent is extended or adjusted under 35 U.S.C. 154(b) by 526 days.

(21) Appl. No.: 13/640,260

(22) PCT Filed: Mar. 4, 2011

(86) PCT No.: PCT/FI2011/050191
§ 371 (c)(1),
(2), (4) Date: Oct. 25, 2012

(87) PCT Pub. No.: WO2011/124747
PCT Pub. Date: Oct. 13, 2011

(65) Prior Publication Data
US 2013/0048022 A1 Feb. 28, 2013

(30) Foreign Application Priority Data
Apr. 9, 2010 (FI) ..................................... 20105363

(51) Int. Cl.
*B08B 1/00* (2006.01)
*B08B 3/04* (2006.01)
(Continued)

(52) U.S. Cl.
CPC ... *B08B 1/00* (2013.01); *B08B 3/04* (2013.01); *G01N 21/15* (2013.01); *G02B 27/0006* (2013.01)

(58) Field of Classification Search
CPC ... G01N 21/00; G01N 21/59; G01N 21/5907; G01N 27/38; G01N 27/416; G01N 21/15; B08B 7/00; B08B 7/02; B08B 3/04; B08B 3/042; B08B 5/02; B08B 2205/00; B08B 2205/005
USPC ............................................ 134/6, 7, 42, 184
See application file for complete search history.

(56) References Cited

U.S. PATENT DOCUMENTS 5,136,882 A    8/1992   Wada
5,597,950 A *   1/1997   Mullen ........................ 73/60.11
(Continued)

FOREIGN PATENT DOCUMENTS

JP    S54110176 U    8/1979
JP    S57-135948 U    8/1982
(Continued)

OTHER PUBLICATIONS

Official Action dated Jul. 4, 2013, in the corresponding to PCT/FI2011/050191.
(Continued)

*Primary Examiner* — Saeed T Chaudhry
(74) *Attorney, Agent, or Firm* — Ladas & Parry LLP

(57) ABSTRACT

An arrangement and method for mechanical cleaning of an active surface (4,17-20) of an instrument (5) in touch with liquid. The active surface of the instrument is exposed to cleaning media (11), which consists of separate, moving particles, enclosed into an instrument container. The motion of the cleaning media is rotational and achieved and maintained by directing an influx (9) parallel to the direction of motion (8) of the cleaning media. The influx may contain gas, liquid or mixture of gas and liquid. The cleaning media wipes clean the at least one active instrument surface.

6 Claims, 6 Drawing Sheets

(51) Int. Cl.
   *G01N 21/15*      (2006.01)
   *G02B 27/00*      (2006.01)

(56) References Cited

U.S. PATENT DOCUMENTS

| | | | |
|---|---|---|---|
| 6,620,255 B1 * | 9/2003 | Dar et al. | 134/1 |
| 2011/0259378 A1 * | 10/2011 | Skeidsvoll et al. | 134/184 |

FOREIGN PATENT DOCUMENTS

| | | | |
|---|---|---|---|
| JP | H07225154 | A | 8/1995 |
| JP | 2002-250711 | A | 9/2002 |
| JP | 2003-098143 | A | 4/2003 |
| JP | 2004-091611 | A | 3/2004 |
| JP | 2004-271211 | | 9/2004 |
| JP | 2004-271211 | A | 9/2004 |
| JP | 2004271211 | A | 9/2004 |
| RU | 2308022 | C2 | 10/2007 |
| SU | 1151870 | A1 | 4/1985 |

OTHER PUBLICATIONS

Chinese Office Action issued Dec. 26, 2013, corresponding to Chinese Patent Application No. 201180018336.5; with English language translation.

Japanese Office Action mailed Dec. 3, 2013 corresponding to Japanese Patent Application No. 2013-503146; with English language translation.

* cited by examiner

ARRANGEMENT AND METHOD FOR MECHANICAL CLEANING OF A TRANSPARENT SURFACE OF AN OPTICAL INSTRUMENT

This application is a 371 of PCT/FI2011/050191 filed on Mar. 4, 2011, which claims priority to Finnish patent application number 20105363, filed on Apr. 9, 2010.

The present invention is related to an arrangement and method for mechanically cleaning of at least one transparent surface of an optical instrument inside a instrument container containing liquid to be processed and/or measured or being an essential component of a process, the instrument container having a cross-section that allows rotating motion of the liquid around a rotation axis, the optical instrument being placed in an aperture in a wall of the instrument container.

When processing various liquids or using them as an essential component of a process there often exist various needs for measuring certain parameters of the liquid, e.g. its density, turbidity, electrical conductivity, pH value etc. There also often exist needs to filtrate or screen the liquid. These measures can be implemented by means of different instruments, e.g. by optically (transparent window), mechanically (screening grid/filters), electro-chemically (electrodes of an electrolysis process) or electrically (conductivity probes) active instruments or an ion selective membrane.

The liquid to be processed or used and/or measured often contains particles or impurities which may deposit on an active surface of an instrument in touch with liquid. This deposition can cause malfunction of the instrument and/or errors in the measuring results, especially when using an optical instrument which requires clear transparent window.

An aim of the present invention is to provide a solution by means of which a transparent surface of an optical instrument inside an instrument container can be cleaned effectively. To this end the arrangement is characterized in that the instrument container is at least partially filled with cleaning media, which consists of separate moving objects, whose material, shape and/or size is selected appropriate to the nature of the surface to be kept clean, that the instrument container is provided with fluid supply means for supplying fluid to drive the liquid and cleaning media to rotating motion inside the instrument container, the cleaning media rotating essentially as a uniform bed, whereby the cleaning media wipes clean the at least one transparent surface being exposed to cleaning media through the instrument aperture. The method of the present invention is characterized in that the instrument container is at least partially filled with cleaning media, which consists of separate moving objects, whose material, shape and/or size is selected appropriate to the nature of the surface to be kept clean, and that fluid is supplied into the instrument container for driving the liquid and cleaning media to rotating motion inside the instrument container the cleaning media rotating essentially as a uniform bed, whereby the cleaning media wipes clean the at least one transparent surface being exposed to cleaning media through the instrument aperture.

By supplying fluid inside the instrument container such that the liquid together with the cleaning media are brought into rotating motion it is possible to keep the surface or surfaces clean continuously, if necessary, by quite low amount of influx. The fluid supply means are preferably provided with control means which are adapted to effect activation or deactivation of the fluid supply means at desired times.

The instrument container can be placed inside a tank or other vessel containing the liquid to be processed and/or measured or being an essential component of a process, or outside such tank or vessel. The instrument container is preferably in fluid connection with the tank or vessel such that the liquid from the tank or vessel can flow or be pumped either continuously or intermittently to the container.

It is possible to place e.g. UV-light and turbidity-sensor to the same instrument container to use the container for different tasks, e.g. destroying microbes and measuring turbidity, either periodically or simultaneously. UV-light can be used also to grow algae on the carrier.

The invention will now be described in more detail with reference to the accompanying drawings, in which.

Figure 3:
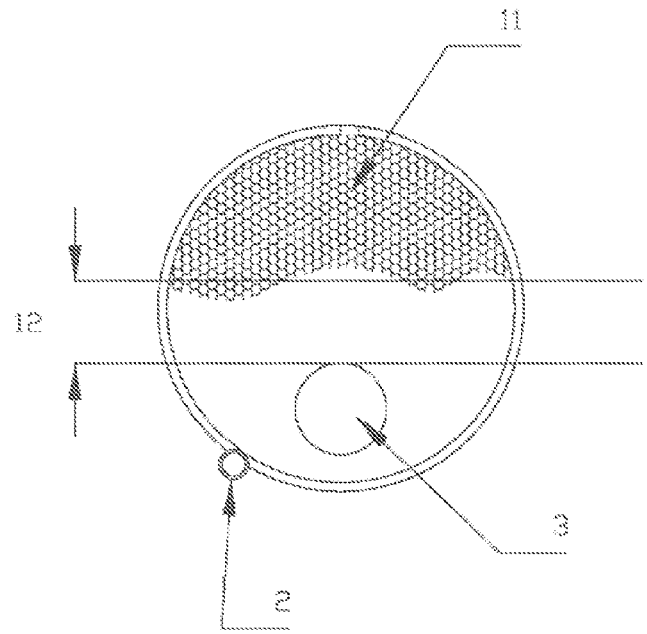
Figure 4:
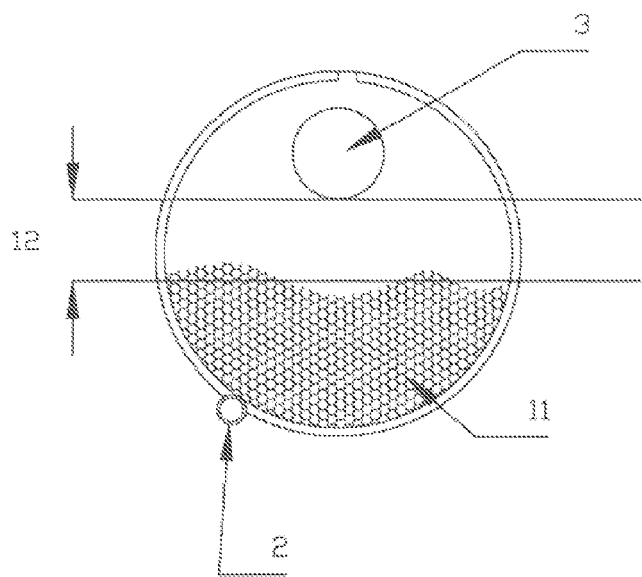
Figure 8:
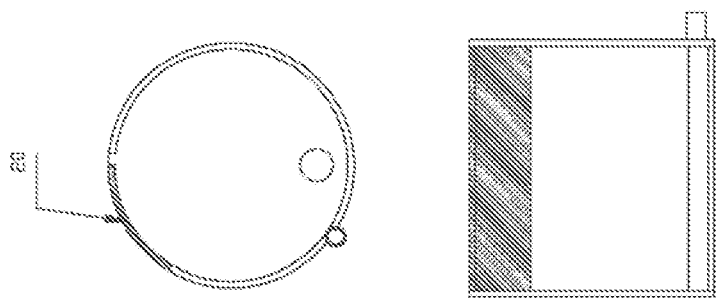
Figure 9:
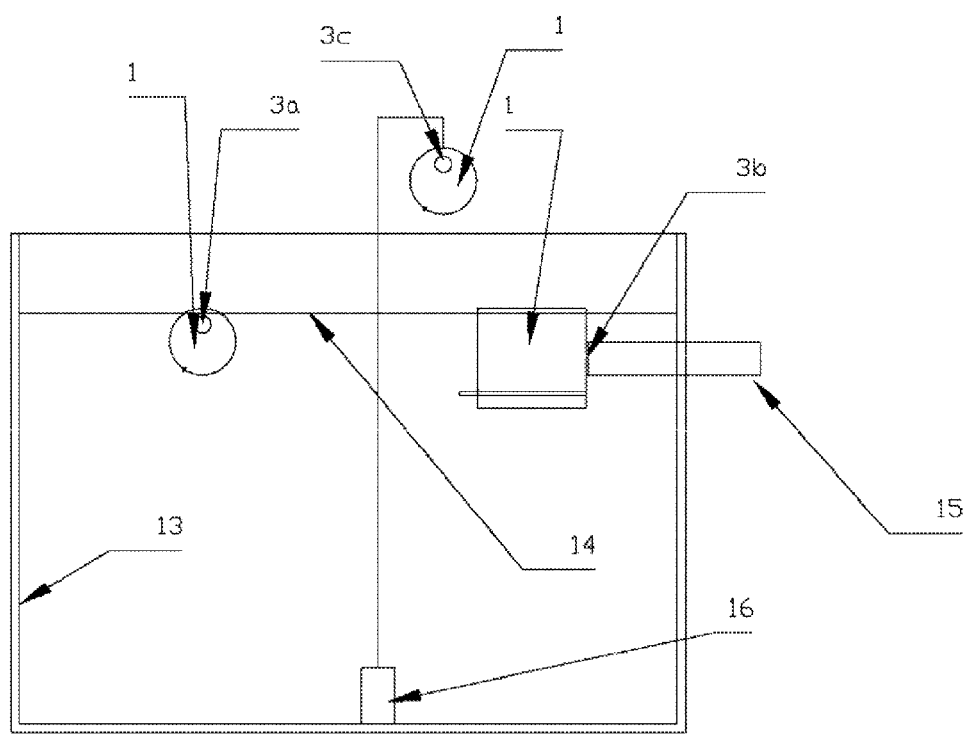
Figure 10:
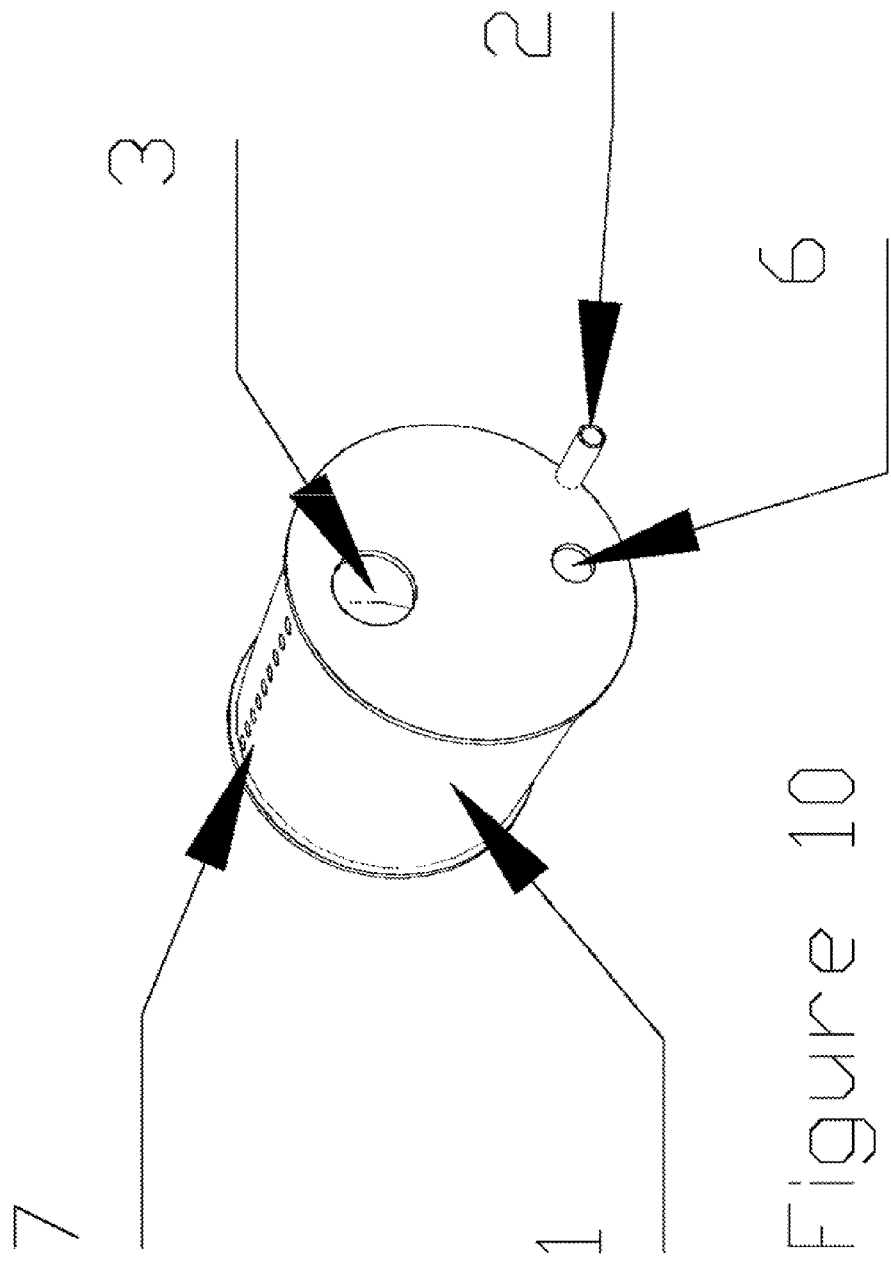

FIGS. 3-4 show two alternative settling sequences of cleaning media in schematic views of principle, and FIGS. 5-8 show four different exemplary surfaces (hatched area) in which the instrument surfaces can be placed, FIG. 9 shows three different exemplary instrument containers placed inside and outside a tank for liquid to be processed and/or measured, and FIG. 10 shows an instrument container in a schematic perspective view.

Figure 11:
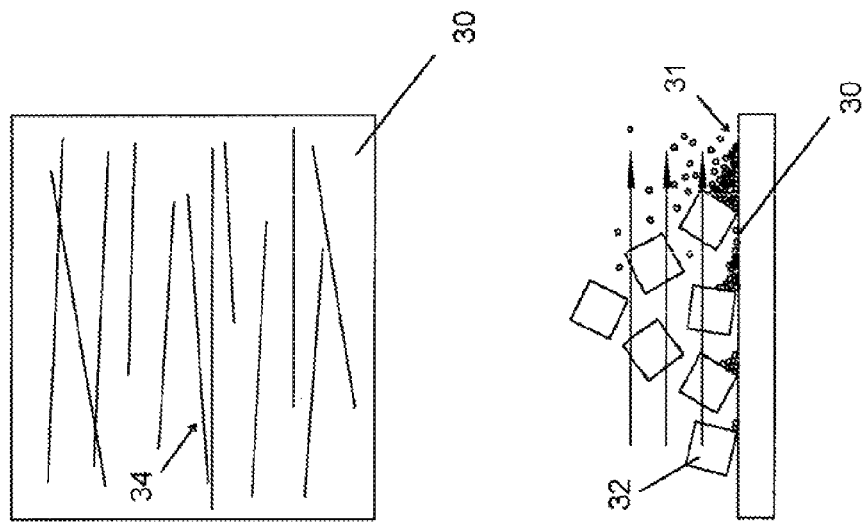

FIG. 11 shows a prior art cleaning process, and

Figure 12:
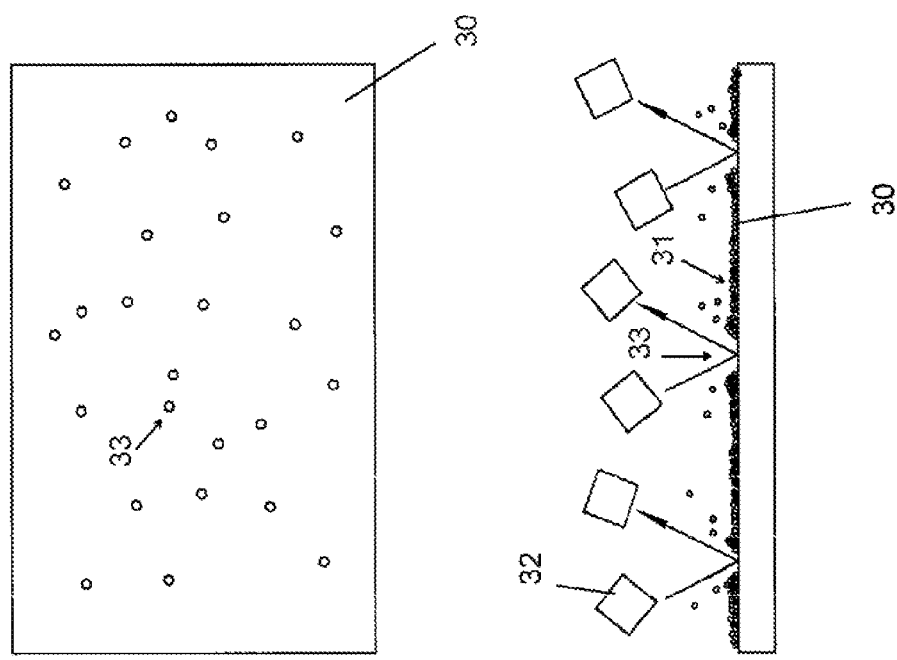

FIG. 12 shows a cleaning process according to the present invention.

Figure 1:
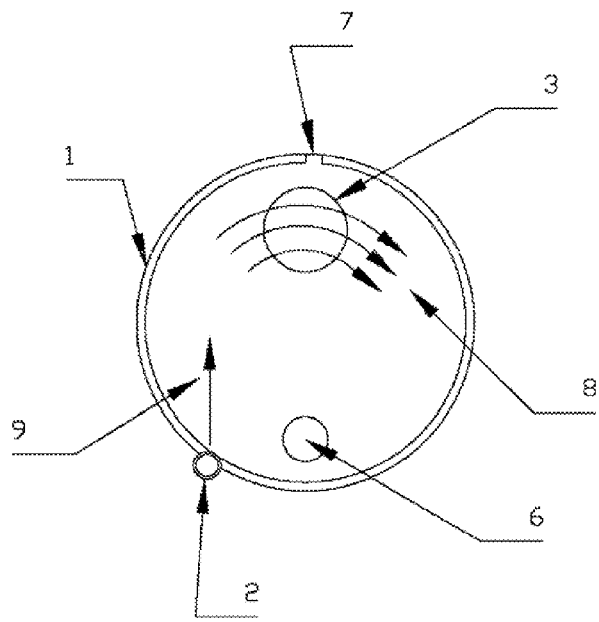
FIG. 1 shows an instrument container in a schematic end view.
Figure 2:
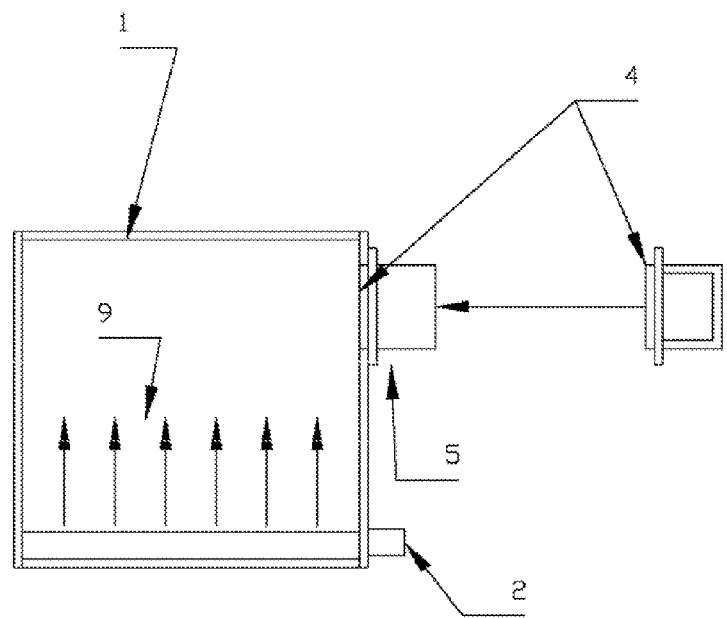
FIG. 2 shows the instrument container of FIG. 1 in a schematic side view.

FIGS. 1-2 show an exemplary instrument container 1. The instrument container is circular in cross-section and it is provided with intake means 6 for the liquid to be measured and/or processed and means 7 for excess outflow, possibly including also particles cleaned from an active surface of an instrument. In FIGS. 1-2 the instrument 5 is disposed in an aperture 3 at the end surface of the instrument container such that the active surface 4 of the instrument faces the liquid in the instrument container. The instrument container includes supply means 2 for fluid to cause the liquid to rotate inside the instrument container. Arrows 9 show influx direction of the fluid and arrows 8 rotating motion of the liquid and a cleaning media therewith. The fluid may be gas, liquid or mixture thereof. The cleaning media consists of separate, moving particles, enclosed into the instrument container. The circular shape of the instrument container allows rotating motion of the cleaning media and minimizes the mutual movement between the cleaning media particles, yet allowing it. The cleaning media forms essentially uniform bed during its rotation and, thus, it wipes the transparent surface to be cleaned quite similarly as a wiper blade, i.e. the cleaning is based on wiping action of the media particles covering together the whole surface to be cleaned. FIG. 12 shows schematically the cleaning media 32 moving along a surface 30 to be cleaned. Dirt 31 deposited on the surface is cleaned effectively by successive media particles 32 in the rotating cleaning media bed. Reference numeral 34 (in the upper part of FIG. 12 shoving the surface 30 from above) shows traces of the wiping action covering essentially the whole surface to be cleaned. FIG. 11 shows schematically a prior art process wherein the cleaning media consist of separate particles 32 colliding randomly with the surface 30 to be cleaned. This cleaning method is quite ineffective since it removes the dirt 31 only point by point. Reference numeral 33 (in the upper part of FIG. 11 shoving the surface 30 from above) shows traces of collisions. This process requires plenty of time to have the whole area cleaned and in a bacteria-rich environment the surface to be cleaned can get dirty again before the whole area is cleaned.

FIG. 10 shows an instrument container corresponding to that of FIGS. 1-2 in a schematic perspective view. The active surface 4 of the instrument 5 is exposed to cleaning media through the instrument aperture 3 and the cleaning media wipes clean the surface 4 when brought into rotating motion. The cleaning media wipes clean also the inner surface of the instrument container. The active instrument surface 5 can be exposed to the cleaning media from through any wall surface of the container 1, or through walls of a separate tube placed on the central axis of the container the instrument being inside the tube. Four exemplary locations are shown in FIGS. 5-8.

Figure 7:
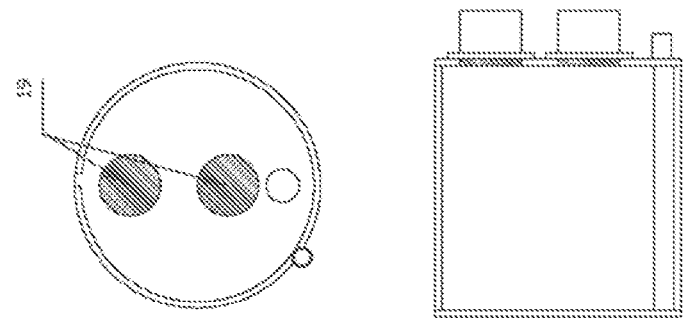
Figure 6:
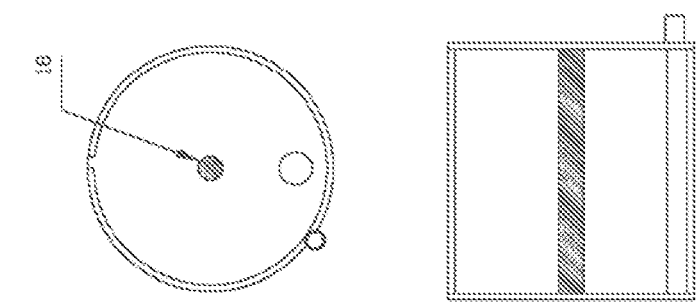
Figure 5:
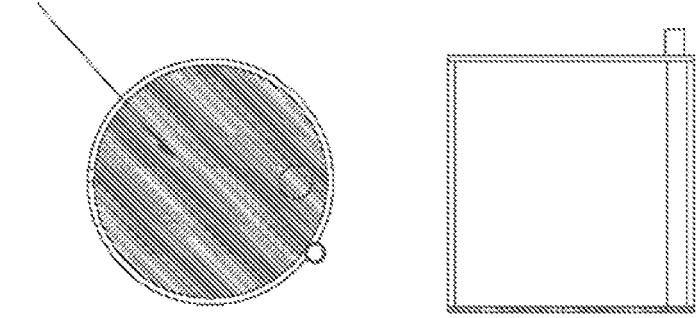

The instrument aperture 3 for the surface 4 of the instrument 5 can be made in any surface of the instrument container. The surface in which the aperture 3 is made can be straight 17, 19 (as shown in FIGS. 5 and 7) or curved 20 along the wall of the instrument container (as shown in FIG. 8) or tubular 18 passing through the container (as shown in FIG. 6). There can be one or more active surfaces to be kept clean in one single instrument container (as shown in FIG. 7).

The cleaning media 11 is preferably arranged to settle to either the bottom or the top of the instrument container for limited period of time. The density difference between the filling liquid and the cleaning media 11 determines whether the media 11 settles to the top (FIG. 3 shows cleaning media having lower density than the liquid) or to the bottom of the instrument container (FIG. 4 shows cleaning media having higher density than the liquid). The cleaning media 11 slows down and eventually stops when the forcing influx is stopped.

The aperture 3 for the instrument 5 must be located so that it does not get covered by the settled cleaning media during the settling phase. In FIGS. 3 and 4 the amount of the cleaning media and the position of the aperture 3 are arranged such that there exists an safety area between the settled cleaning media and the aperture 3 providing safety tolerance for the cleaning media not to cover the aperture 3 during the measurement phase.

All open apertures of the instrument container walls must be smaller than a single particle of the cleaning media or there must be some other method to prevent the cleaning media from escaping the instrument container.

FIG. 9 shows two different exemplary instrument containers 1 placed in a tank 13 for a liquid to be processed and/or measured or used as an essential component of a process and one exemplary instrument container placed outside the tank. Instrument 3a is an optical probe for measuring, e.g. turbidity of the liquid and instrument 3b is a particle screening grid. Filtrated liquid is removed via the outlet 15. The surface of the liquid is marked by 14. Pump 16 is arranged inside the tank 13 to pump the liquid to an exterior instrument container 1 having an instrument 3c, e.g. an optical probe.

The above disclosure of the present invention is given only as exemplar of preferred embodiments thereof and it is not intended to limit the scope of protection as defined in the claims. For example, the instrument container may have different cross-sections than circular by having its internal surface made essentially smooth, allowing for unhindered rotation of the cleaning media around a rotation axis. It is also possible to combine several instrument containers into a single unit having a fluid connection between the containers.

The cleaning media can have also other functions than cleaning active instrument surfaces, e.g. it can include a color changing agent to show, e.g. temperature change of the liquid to be examined or presence of certain solute therein.

The invention claimed is:

1. An arrangement for mechanically cleaning of at least one transparent surface of an optical instrument inside an instrument container containing liquid to be measured, the instrument container having a circular or elliptical cross-section that allows rotating motion of the liquid around a rotation axis, the optical instrument being placed in an aperture in a wall of the instrument container, wherein the instrument container is at least partially filled with cleaning media, wherein the cleaning media comprises separate moving objects, wherein at least one of material, shape and size of the moving objects is selected appropriate to the nature of the surface to be kept clean, the instrument container being provided with fluid supply means for supplying fluid to drive the liquid and cleaning media to rotating motion inside the instrument container, the cleaning media forming an essentially uniform bed during rotation of the moving objects with the cleaning media, whereby the cleaning media wipes clean the at least one transparent surface being exposed to cleaning media through the instrument aperture, wherein the cleaning media has a different density than a filling liquid such that the cleaning media can settle to either a bottom or a top of the instrument container for a limited period of time when stopping the forcing influx, and that an amount of the cleaning media and the position of the aperture are arranged such that there exists a safety area between the settled cleaning media and the aperture, providing safety tolerance for the cleaning media not to cover the aperture during the measurement phase.

2. The arrangement as set forth in claim 1, wherein the fluid is gas, liquid, or mixture thereof.

3. The arrangement as set forth in claim 1, wherein the instrument container is an elongated tubular or discoid structure disposed in an essentially horizontal position.

4. The arrangement as set forth in claim 1, wherein the instrument container has a structure which is essentially spherical or ellipsoid generated by rotation.

5. The arrangement as set forth in claim 1, wherein the cleaning media includes a color changing agent.

6. A method for mechanically cleaning of at least one transparent surface of an optical instrument inside a instrument container containing liquid to be measured, the instrument container having a circular or elliptical cross-section that allows rotating motion of the liquid around a rotation axis, the optical instrument being placed in an aperture in a wall of the instrument container, wherein the instrument container is at least partially filled with cleaning media, which consists of separate moving objects, wherein at least one of material, shape and size of the moving objects is selected appropriate to the nature of the surface to be kept clean, in which method, fluid is supplied into the instrument container for driving the liquid and cleaning media to rotating motion inside the instrument container, the cleaning media forming an essentially uniform bed during rotation of the moving objects with the cleaning media, whereby the cleaning media wipes clean the at least one transparent surface being exposed to cleaning media through the instrument aperture, wherein the cleaning media is arranged to settle to either a bottom or a top of the instrument container for a limited period of time when stopping the forcing influx for the cleaning media, the amount of the cleaning media and the position of the aperture being arranged such that there exists a safety area between the settled cleaning media and the aperture, providing safety tolerance for the cleaning media not to cover the transparent surface of the optical instrument during the optical measurement phase.

* * * * *